United States Patent [19]

Hatton

[11] Patent Number: 4,871,748
[45] Date of Patent: Oct. 3, 1989

[54] PHENYLPROPARGYLAMINE DERIVATIVES

[75] Inventor: Leslie R. Hatton, Chelmsford, England

[73] Assignee: May & Baker Limited, England

[21] Appl. No.: 693,729

[22] Filed: Jan. 23, 1985

[30] Foreign Application Priority Data

Feb. 8, 1984 [GB] United Kingdom ................. 8403362
Dec. 12, 1984 [GB] United Kingdom ................. 8431375

[51] Int. Cl.$^4$ .................. C07F 237/30; C07F 237/00; C07F 9/02; A61K 39/445
[52] U.S. Cl. .................................. 514/317; 514/331; 514/822; 546/229; 546/232; 546/236; 546/237; 546/238; 546/239; 546/240
[58] Field of Search ........................ 514/317, 331, 822; 546/240, 238, 229, 232, 236, 239, 237

[56] References Cited

U.S. PATENT DOCUMENTS

| 4,285,957 | 8/1981 | Carr et al. ........................... 514/317 |
| 4,347,252 | 8/1982 | Leftwick et al. .................... 546/192 |
| 4,634,699 | 1/1987 | McDermed et al. ................. 544/41 |

Primary Examiner—Glennon H. Hollrah
Assistant Examiner—Raymond Covington
Attorney, Agent, or Firm—Scully, Scott, Murphy & Presser

[57] ABSTRACT

Compounds of the formula:

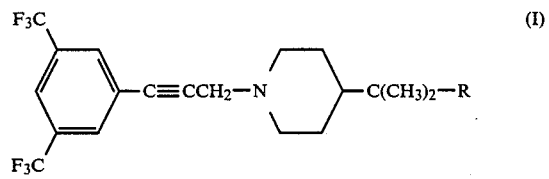

wherein R represents hydroxymethyl, alkoxymethyl of 2 to 6 carbon atoms, optionally substituted phenoxymethyl, alkanoyloxymethyl of 3 to 10 carbon atoms, optionally substituted benzoyloxymethyl, alkylsulphonyloxymethyl of 2 to 9 carbon atoms, optionally substituted phenylsulphonyloxymethyl, formyl, aminomethyl optionally substituted by 1 or 2 alkyl groups of 1 to 4 carbon atoms, or hydroxyiminomethyl, and acid addition salts thereof, are useful as rodenticides.

17 Claims, No Drawings

PHENYLPROPARGYLAMINE DERIVATIVES

DESCRIPTION

This invention relates to new useful phenylpropargylamine derivatives and acid addition salts thereof, to processes for their preparation, and to compositions containing them suitable for oral ingestion by, and killing of, warm-blooded vermin.

The compounds of the present invention are the phenylpropargylamine derivatives of general formula I herein depicted wherein R represents the hydroxymethyl group, a straight- or branched-chain alkoxymethyl group containing from 2 to 6 carbon atoms, an optionally substituted phenoxymethyl group, a straight- or branched-chain alkanoyloxymethyl group containing from 3 to 10 carbon atoms, an optionally substituted benzoyloxymethyl group, a straight- or branched-chain alkylsulphonyloxymethyl group containing from 2 to 9 carbon atoms, an optionally substituted phenylsulphonyloxymethyl group, the formyl group, an aminomethyl group optionally substituted by one or two straight- or branched-chain alkyl groups, which may be the same or different and each contain from 1 to 4 carbon atoms, or the hydroxyiminomethyl group and acid addition salts thereof. The acid addition salts may be formed with inorganic acids, for example hydrochloric, sulphuric, phosphoric, nitric or sulphamic acid, or with organic acids, for example acetic, octanoic, methanesulphonic, glutamic or 2-hydroxyethanesulphonic acid.

Optionally substituted phenyl moieties in the present specification may be substituted by one or more substituents selected from halogen atoms, the trifluoromethyl group and straight- or branched-chain alkyl and alkoxy groups containing from 1 to 4 carbon atoms.

Preferred compounds of general formula I are those wherein R represents the hydroxymethyl group, a straight- or branched-chain alkoxymethyl group containing from 2 to 6 carbon atoms, a straight- or branched-chain alkanoyloxymethyl group containing from 3 to 7 carbon atoms, an optionally substituted benzoyloxymethyl group, a straight- or branched-chain alkylsulphonyloxymethyl group containing from 2 to 6 carbon atoms, the formyl group or the hydroxyiminomethyl group.

The compounds of general formula I and their acid addition salts are highly toxic to warm-blooded animals, more especially rodents, e.g. rats and mice, by oral administration and may be used to kill warm-blooded vermin, i.e. undesired warm-blooded animals, for example to control rodent infestations. Where reference is made in the present specification to the use of the compounds of general formula I to kill warm-blooded vermin, for example as rodenticides, it is to be understood that such reference is intended to include also the acid addition salts of the compounds of general formula I.

The following compounds of general formula I are of particular interest for killing warm-blooded vermin by oral administration:

Compound No.
1. 1-(3,5-bistrifluoromethylphenyl)-3-[4-(1,1-dimethyl-2-hydroxyethyl)piperidino]prop-1-yne
2. 1-(3,5-bistrifluoromethylphenyl)-3-[4-(1,1-dimethyl-2-methoxyethyl)piperidino]prop-1-yne
3. 1-(3,5-bistrifluoromethylphenyl)-3-[4-(1,1-dimethyl-2-acetyloxyethyl)piperidino]prop-1-yne
4. 1-(3,5-bistrifluoromethylphenyl)-3-[4-(1,1-dimethyl-2-oxoethyl)piperidino]prop-1-yne
5. 1-(3,5-bistrifluoromethylphenyl)-3-[4-(1,1-dimethyl-2-benzoyloxyethyl)piperidino]prop-1-yne
6. 1-(3,5-bistrifluoromethylphenyl)-3-[4-(1,1-dimethyl-2-hydroxyiminoethyl)piperidino]prop-1-yne
7. 1-(3,5-bistrifluoromethylphenyl)-3-[4-(1,1-dimethyl-2-methylsulphonyloxyethyl)piperidino]prop-1-yne The utility of the compounds of general formula I as rodenticides is demonstrated by the following test:

Test

Acute Oral Toxicity in Mice (Laboratory Strain)

Groups of mice were dosed orally with graded doses of the test compound in aqueous suspension and observed until there had been no deaths for at least three days. The acute oral LD50, that is to say the dose in mg/kg animal body weight necessary to kill 50% of the mice, was determined from the numbers of animals for each dose which died during the observation period by reference to published tables.

| Compound No | LD50 | Observations |
|---|---|---|
| 1 (as free base) | 78 | There were no marked signs of poisoning prior to death at between 5 and 6 days after dosing. |
| 1 (as hydrochloride) | 62 | |
| 2 (as hydrochloride) | 68 | |
| 3 (as hydrochloride) | 68 | |
| 4 (as hydrochloride) | 68 | |
| 1 (as nitrate) | 72 | |
| 1 (as acetate) | 95 | |
| 1 (as sulphamate) | 72 | |

The compounds of general formula I may be prepared by the application or adaptation of known methods for the preparation of phenylpropargylamine derivatives, for example by one of the following processes:

(1) The reaction of a compound of general formula II herein depicted (wherein X represents a halogen, preferably iodine or bromine, atom) with a compound of general formula III herein depicted (wherein R' represents the hydroxymethyl group, a straight- or branched-chain alkoxymethyl group containing from 2 to 6 carbon atoms, an optionally substituted phenoxymethyl group, a straight- or branched-chain alkanoyloxymethyl group containing from 3 to 10 carbon atoms, an optionally substituted benzoyloxymethyl group, a straight- or branched-chain alkylsulphonyloxymethyl group containing from 2 to 9 carbon atoms or an optionally substituted phenylsulphonyloxymethyl group).

The reaction between a compound of general formula II and a compound of general formula III may be effected in the presence of a copper (I) salt, preferably cuprous iodide, and in the presence of (a) dichlorobis(triphenylphosphine)palladium (II) and, optionally, a triarylphosphine, preferably tri-o-tolylphosphine or triphenylphosphine, or (b) a palladium (II) compound, preferably palladium acetate, and a triarylphosphine, preferably tri-o-tolylphosphine or triphenylphosphine. The reaction may be effected, optionally in the presence of an inert organic solvent, for example acetonitrile, in the presence of an organic base, for example diethylamine, and at a temperature of from ambient temperature to the reflux temperature of the reaction mixture. The organic base may conveniently serve as the solvent in the foregoing process.

(2) The reaction of a compound of general formula IV herein depicted (wherein $M^1$ represents a hydrogen atom or an alkali metal, for example sodium, potassium or lithium, atom or alkaline earth metal, for example magnesium, atom or a copper, silver or zinc atom) with a compound of general formula V herein depicted (wherein R" represents the hydroxymethyl group or an aminomethyl group optionally substituted by one or two straight- or branched-chain alkyl groups, which may be the same or different and each contain from 1 to 4 carbon atoms, and Y represents a hydrogen atom when the symbol $M^1$ in general formula IV represents a hydrogen atom or Y represents a halogenomethylene, $C_{1-4}$alkoxymethylene, chloromercuriomethylene or alkyl- or aryl- sulphonyloxymethylene, e.g. tosyloxymethylene, group when the symbol $M^1$ in general formula IV represents a metal atom) and, when the symbol $M^1$ in general formula IV represents a hydrogen atom, i.e. when the compound of general formula IV is of the formula VI herein depicted, a source of formaldehyde.

When the compound of general formula IV is the compound of formula VI, the reaction with the compound of general formula V and the source of formaldehyde, for example paraformaldehyde or formalin, may be effected in the presence of a copper (I) salt, preferably cuprous chloride, in an inert organic solvent, for example dioxan, and at a temperature of from ambient temperature to the reflux temperature of the reaction mixture, and preferably at 100° C.

When the compound of general formula IV is not the compound of formula VI, the reaction with the compound of general formula V in the absence of a source of formaldehyde may be effected in an inert organic solvent at a temperature of from 0° C. to the reflux temperature of the reaction mixture.

(3) The reaction of a compound of general formula VII herein depicted (wherein Z represents a chlorine, bromine or iodine atom or an alkylsulphonyloxy or arylsulphonyloxy, for example tosyloxy, group) with a compound of general formula VIII herein depicted (wherein R''' represents the hydroxymethyl group, a straight- or branched-chain alkoxymethyl group containing from 2 to 6 carbon atoms or an optionally substituted phenoxymethyl group, and $M^2$ represents an alkali metal, preferably lithium, atom or when the symbol Z in general formula VII represents a chlorine, bromine or iodine atom, $M^2$ may additionally represent a hydrogen atom).

The reaction may be effected in the presence of an inert organic solvent, preferably diethyl ether of tetrahydrofuran when the symbol $M^2$ in general formula VIII represents an alkali metal atom, or for example acetone when the symbol $M^2$ in general formula VIII represents a hydrogen atom.

When the symbol $M^2$ in general formula VIII represents a hydrogen atom, the reaction may be effected in the presence of an inorganic base, for example potassium carbonate, and at a temperature of from ambient temperature to the reflux temperature of the reaction mixture.

(4) When R represents a straight- or branched-chain alkanoyloxymethyl group containing from 3 to 10 carbon atoms, an optionally substituted benzoyloxymethyl group, a straight- or branched-chain alkylsulphonyloxymethyl group containing from 2 to 9 carbon atoms, or an optionally substituted phenylsulphonyloxymethyl group, by the reaction of the compound of general formula I wherein R represents the hydroxymethyl group with the appropriate alkanoyl or benzoyl halide or alkylsulphonyl or phenylsulphonyl halide (preferably chloride or bromide). The reaction may be effected in the absence or presence of an inert organic solvent, E.G. dichloromethane or tetrahydrofuran, optionally in the presence of an acid acceptor, E.G triethylamine, and at a temperature of from 0° C. to the reflux temperature of the reaction mixture.

(5) When R represents the formyl group, by the oxidation of the compound of general formula I wherein R represents the hydroxymethyl group with a suitable oxidant such as pyridinium chlorochromate in an inert organic solvent, for example, dichloromethane, at a temperature of from 0° C. to the reflux temperature of the reaction mixture.

(6) When R represents an aminomethyl group optionally substituted by one or two straight- or branched-chain alkyl groups, which may be the same or different and each contain from 1 to 4 carbon atoms, by the reaction of a compound of general formula I wherein R represents a straight- or branched-chain alkylsulphonyloxymethyl group containing from 2 to 9 carbon atoms, or an optionally substituted phenylsulphonyloxymethyl group with ammonia or the appropriate amine.

(7) When R represents the hydroxyiminomethyl group, by the reaction of the compound of general formula I wherein R represents the formyl group with a salt of hydroxylamine. The reaction may be effected in the presence of an inert organic solvent, E.G. ethanol, optionally in the presence of an acid acceptor, E.G. triethylamine, and at a temperature of from ambient temperature to the reflux temperature of the reaction mixture.

A compound of general formula III may be prepared by the reaction of the compound of general formula V wherein Y represents a hydrogen atom (viz. 4-(1,1-dimethyl-2-hydroxyethyl)piperidine) with 1-bromoprop-2-yne, or, conveniently, 1-chloroprop-2-yne in the presence of an inorganic or organic base, for example potassium carbonate or an excess of the compound of general formula V wherein Y represents a hydrogen atom.

The reaction may be effected optionally in the presence of an inert organic solvent, for example methanol, acetone or acetonitrile.

Compounds of general formula VII may be prepared by the application or adaptation or methods described in the chemical literature, for example, where Z represents an iodine atom, by S. Wallat & W. H. Kunau, Chem. Phys. Lipids 13, 159 (1974); where Z represents a bromine atom, by R. Matchinek & W. Luttke, Synthesis, 1975, 255; and where Z represents a chlorine atom, by M. J. Murray, J. Amer. Chem. Soc., 2662, (1938).

Acid addition salts may be prepared from the compounds of general formula I by methods known per se, for example by reaction of stoichiometric quantities of the compound of general formula I and the appropriate acid, e.g. an inorganic acid such as hydrochloric, sulphuric, phosphoric, nitric or sulphamic acid, or an organic acid such as acetic, octanoic, methanesulphonic, glutamic or 2-hydroxyethanesulphonic acid, in a suitable solvent, e.g. diethyl ether, ethyl acetate or acetone. The acid addition salts may be purified by recrystallization from one or two or more suitable solvents. Acid addition salt formation provides a means of obtaining the compounds of general formula I in pure form.

Compounds of general formulae II, III, IV, V and VIII may be prepared by methods known per se.

By the term "methods known per se" as used in the present specification is meant methods heretofore used or described in the chemical literature.

The following Examples and Reference Examples illustrate the present invention. Where reference is made to medium pressure liquid chromatography, the pressure employed was from 5 to 10 pounds per square inch and the support was silica (Merck type 9385; 230–400 mesh).

EXAMPLE 1

Compound No. 1

Triphenylphosphine (10 mg), copper (I) iodide (5 mg) and dichlorobis(riphenylphosphine)palladium (8.75 mg) were dissolved, with gentle heating, in triethylamine (5 ml). The solution thus obtained was cooled to laboratory temperature and 3-[4-(1,1dimethyl-2-hydroxyethyl)piperidino]prop-1-yne (0.97 g) was added with stirring. The stirred mixture was heated under reflux and 3,5-bistrifluoromethylbromobenzene [which may be prepared as described by E. T. McBee et al, J. Amer. Chem. Soc. (1950), 72, 1651; 1.47 g] was added. After heating under reflux for 15 minutes, the reaction mixture was filtered. The precipitate was washed with cold triethylamine (5 ml). The filtrate and washings were evaporated to give a brown crystalline solid which was stirred with n-hexane (50 ml) for 30 minutes. The n-hexane solution was then decanted and the residue was washed with further n-hexane (50 ml). The n-hexane solution was decanted and the combined n-hexane solutions were evaporated to dryness, to give a pale yellow crystalline solid (1.92 g), m.p. 71°–76° C., which was subjected to medium pressure liquid chromatography [elution solvent dichloromethane:methanol (95:5 by volume)], to give 1-(3,5-bistrifluoromethylphenyl)3-[4-(1,1-dimethyl-2-hydroxyethyl)piperidino]prop-1-yne (1.56 g), m.p. 85°–87° C., in the form of beige crystals.

EXAMPLE 2

Compound No. 2

Triphenylphosphine (0.076 g), cuprous iodide (0.033 g) and bis-triphenylphosphine palladium dichloride (0.067 g) was added to triethylamine (38 ml) and heated at 40° C. with magnetic stirring. 3-[4-(1,1-dimethyl-2-methoxyethyl)piperidino]prop-1-yne (7.9 g) was added. After the addition of 3,5-bistrifluoromethyl-bromobenezene (11.1 g), the solution was heated at 80° C. for 1 hour, and left overnight at room temperature. The precipitated solid was filtered off and washed with dry diethyl ether (50 ml). The filtrate and washings were evaporated in vacuo to give a brown oil after further evaporation of added toluene. After the addition of petroleum ether (b.p. 60°–80° C.) and filtration to remove a little tar, the solution was brought to pH1 by the addition of ethereal hydrogen chloride solution. The buff solid which precipitated was filtered off, washed with petroleum ether (b.p. 60°–80° C.) and dried to give 1-(3,5-bistrifluoromethylphenyl)-3-[4-(1,1-dimethyl-2-methoxyethyl)piperidino]prop-1-yne hydrochloride (10.3 g) as a buff solid m.p. 169°–170° C.

EXAMPLE 3

Compound No. 3

Acetyl chloride (5 ml) was added to 1-(3,5-bistrifluoromethylphenyl)-3-[4-(1,1-dimethyl-2-hydroxyethyl)piperidino]prop-1-yne (1.5 g) with swirling. An exothermic reaction occurred to give a product which quickly solidified. After 1 hour this solid was added to ice (30 ml) and then extracted with diethyl ether (50 ml). The extract was brought to basic pH with saturated aqueous sodium carbonate solution, and the ethereal layer was collected. The aqueous phase was re-extracted with diethyl ether (50 ml), and the combined ethereal solution was dried over anhydrous magnesium sulphate, filtered and evaporated in vacuo to give a yellow oil (1.7 g). This oil was dissolved in diethyl ether (20 ml) and excess ethereal hydrogen chloride solution was added. The colourless solid which precipitated was filtered off and recrystallised from a mixture of isopropyl alcohol and diethyl ether to give 1-(3,5-bistrifluoromethylphenyl)-3-[4-(1,1-dimethyl-2-acetyloxyethyl)piperidino]prop-1-yne hydrochloride (1.1 g) in the form of colourless crystals m.p. 182°–184° C.

EXAMPLE 4

Compound No. 4

A solution of 1-(3,5-bistrifluoromethylphenyl)-3-[4-(1,1-dimethyl-2-hydroxyethyl)piperidino]prop-1-yne (3.0 g) in dichloromethane (20 ml) was added to a stirred mixture of pyridium chlorochromate (1.75 g) and dichloromethane (20 ml) under anhydrous conditions. After 4.5 hours stirring, the reaction was complete, and dry diethyl ether (60 ml) was added. After filtration twice, the solution was evaporated in vacuo to give a brown solid (2.7 g). This solid was chromatographed on silica gel (Merck; 0.04–0.063 mm) using medium pressure and eluting with a mixture of dichloromethane and ethyl acetate (1:1) to give the product as a yellow oil (0.9 g). Ethereal hydrogen chloride solution was added to an ethereal solution of this oil to pH1, and the precipitated white solid was filtered off after dilution with petroleum ether (b.p. 60°–80° C.; 30 ml) to give after drying 1-(3,5-bistrifluoromethylphenyl)-3-[4-(1,1-dimethyl-2-oxoethyl)piperidino]prop-1-yne hydrochloride (1.0 g) m.p. 184°–186° C. with decomposition.

EXAMPLE 5

Acid addition salts of Compound No. 1

(i) A solution of 1-(3,5-bistrifluoromethylphenyl)-3-[4-(1,1-dimethyl-2-hydroxyethyl)piperidino]-prop-1-yne (2.0 g) in a mixture of diethyl ether (20 ml) and dichloromethane (5 ml) was treated with a solution of concentrated sulphuric acid in diethyl ether (1:25v/v; 13 ml) with magnetic stirring. After evaporation of the solvent in vacuo, and drying in vacuo at 0.3 mm Hg, 1-(3,5-bistrifluoromethylphenyl)-3-[4-(1,1-dimethyl-2-hydroxyethyl)piperidino]prop-1-yne sulphate (2.4 g) was obtained as a buff semi-solid.

(ii) A solution of 1-(3,5-bistrifluoromethylphenyl)-3-[4-(1,1-dimethyl-2-hydroxyethyl)piperidino]prop-1-yne (2.0 g) in dry acetone (20 ml) was treated with an aqueous nitric acid solution (0.25M; 19.6 ml) with magnetic stirring. The solvent was evaporated in vacuo, and the residue was dried at 0.3 mm Hg to give 1-(3,5-bistrifluoromethylphenyl)-3-[4-(1,1-dimethyl-2-hydroxyethyl)piperidino]prop-1-yne nitrate (2.28 g) as a brown solid.

(iii) A solution of 1-(3,5-bistrifluoromethylphenyl)-3-[4-(1,1-dimethyl-2-hydroxyethyl)piperidino]-prop-1-yne (2.0 g) in dry diethyl ether (20 ml) containing a few drops of ethanol, was brought to pH 1 with an ethereal solution of hydrogen chloride gas. The resulting solution was diluted to 40 ml with petroleum ether (b.p. 60°–80° C.), a buff solid was filtered off, washed with a 1:1 solution of diethyl ether and petroleum ether (25 ml), and dried to give 1-(3,5-bistrifluoromethylphenyl)-3-[4-(1,1-dimethyl-2-hydroxyethyl)piperidino]-prop-1yne hydrochloride (2.1 g) m.p 183°–185° C. as buff crystals.

By proceeding in a similar manner to that hereinbefore described in (ii) above.

(iv) An aqueous solution of sulphamic acid (0.0237% w/v; 20 ml) was used as the acid component, to give 1-(3,5-bistrifluoromethylphenyl)-3-[4-(1,1-dimethyl-2-hydroxyethyl)piperidino]prop-1-yne sulphamate (2.42 g) as a brown oil.

(v) A solution of acetic acid in diethyl ether (0.014% w/v; 20 ml) was used as the acid component, to give 1-(3,5-bistrifluoromethylphenyl)-3-[4-(1,1-dimethyl-2-hydroxyethyl)piperidino]prop-1-yne acetate (2.24 g) as a red solid.

(vi) A solution of orthophosphoric acid in diethyl ether (0.027% w/v; 20 ml) was used as acid component, to give 1-(3,5-bistrifluoromethylphenyl)-3-[4-(1,1-dimethyl-2-hydroxyethyl)piperidino]prop-1-yne phosphate (2.47 g) as an orange gum.

EXAMPLE 6

Compound No. 5

Triethylamine (1.2 ml) was added to a solution of 1-(3,5-bistrifluoromethylphenyl)-3-[4-(1,1-dimethyl-2-hydroxyethyl)piperidino]prop-1-yne (3.5 g) in dichloromethane (25 ml) with mechanical stirring. Benzoyl chloride (1.2 g) was slowly added during 15 minutes and then refluxed for 4 hours. After cooling to room temperature additional benzoyl chloride (1.2 g) was added, and reflux resumed for a further 1½ hours. After cooling the mixture was added to excess aqueous sodium bicarbonate solution, and heated on the steambath for 2 hours. After cooling, the mixture was extracted with dichloromethane, dried over anhydrous magnesium sulphate, and evaporated in vacuo to give a red oil (4.3 g). This oil was chromatographed on silica gel (Merck) eluting with a mixture of dichloromethane and methanol (95:5) under medium pressure to give 1-(3,5-bistrifluoromethylphenyl)-3-[4-(1,1-dimethyl-2-benzoyloxyethyl)piperidino]prop-1-yne (3.0 g) as a brown oil.

EXAMPLE 7

Compound No. 6

Triethylamine (0.4 ml), followed by hydroxylamine hydrochloride (0.18 g) were added to a stirred solution of 1-(3,5-bistrifluoromethylphenyl)-3-[4-(1,1-dimethyl-2-oxoethyl)peperidino]prop-1-yne (1.0 g) in ethanol (10 ml). The mixture was left overnight at room temperature, and then heated under reflux conditions for 2 hours. After cooling, and evaporation of the solvent, the dark orange solid was chromatographed on silica gel (Merck). Elution with a mixture of dichloromethane and ethyl acetate (95:5) under medium pressure gave 3-[4-(1,1-dimethyl-2-hydroxyiminoethyl)piperidino]-1-(3,5-bistrifluoromethylphenyl)prop-1-yne, a buff gum which slowly solidified (0.9 g), m.p. 63°–65° C.

EXAMPLE 8

Compound No. 7

Triethylamine (0.75 g), followed by methylsulphonyl chloride (0.85 g) were added to a solution of 1-(3,5-bistrifluoromethylphenyl)-3-[4-(1,1-dimethyl-2-hydroxyethyl)piperidino]-prop-1-yne (3.0 g) in tetrahydrofuran (50 ml). After stirring for 5 hours, the precipitate of triethylamine hydrochloride was filtered off, and the filtrate was evaporated in vacuo to give a brown gum. This gum was purified by medium pressure chromatography using a mixture of dichloromethane and ethyl acetate (85:15) as eluent to give 1-(3,5-bistrifluoromethylphenyl)-3-[4-(1,1-dimethyl-2-methylsulphonyloxyethyl)piperidino]prop-1-yne (2.4 g) as a colourless gum.

REFERENCE EXAMPLE 1

3-[4-(1,1-dimethyl-2-hydroxyethyl)piperidino]prop-1-yne (used as a starting material in Example 1) was prepared as follows:

4-(1,1-dimethyl-2-hydroxyethyl)piperidine acetate (1.6 g) was added, with stirring, to 10% weight-volume aqueous sodium hydroxide solution (6 ml) and propargyl chloride (0.56 ml) was then added with stirring at laboratory temperature. Stirring was continued for six hours at laboratory temperature and the reaction mixture was then filtered to give an oily solid which was then dissolved in diethyl ether (50 ml). The ethereal solution was dried over anhydrous magnesium sulphate, filtered and evaporated to give a dark yellow oil (1 g), which was recrystallised from petroleum ether (b.p. 60°–80° C.), to give 3-[4-(1,1-dimethyl-2-hydroxyethyl)piperidino]prop-1-yne (0.82 g), m.p. 78°–82° C., in the form of pale yellow crystals.

REFERENCE EXAMPLE 2

4-(1,1-Dimethyl-2-hydroxyethyl)piperidine acetate (used as a starting material in Reference Example 1) was prepared as follows:

4-(1,1-Dimethyl-2-hydroxyethyl)pyridine [which may be prepared as described by Fraenkel et al, J. Amer. Chem. Soc. (1971), 93, 7228; 3 g] was dissolved in acetic acid (30 ml) and hydrogenated in the presence of platinum oxide catalyst for 10 hours at a maximum temperature of 37° C. and a pressure of 50 pounds per square inch, until 100% of the theoretical uptake of hydrogen had occurred. The reaction mixture was then filtered and the filtrate was evaporated under reduced pressure (15 mmHg) to give a pale yellow oil, which was then distilled (b.p. 120° C./0.2 mmHg) to give a colourless oil, which was recrystallised from a mixture of ethanol and diethyl ether to give 4-(1,1-dimethyl-2-hydroxyethyl)piperidine acetate (1.8 g), m.p. 108°–110° C., in the form of colourless crystals.

REFERENCE EXAMPLE 3

A 10% w/v aqueous sodium hydroxide solution (22 ml) was added to 4-(1,1-dimethyl-2-methoxyethyl)-piperidine (9.6g) at room temperature with stirring. Propargyl chloride (3.8 ml) was added in one portion and the mixture was stirred mechanically overnight. After 2 days at room temperature the solution was diluted with excess water and extracted with dichloromethane (3×50 ml). The organic phase was washed with water, dried over anhydrous magnesium sulphate and evaporated in vacuo to give a brown oil (10.2 g). A sample of this oil was chromatographed on silica gel (Merck; 0.04–0.063 mm) under medium pressure eluting with a mixture of ethyl acetate and dichloromethane (1:1) to give a almost colourless oil (2.6 g). A solution of this oil in dry diethyl ether was brought to pH1 with added ethereal hydrogen chloride solution to give an oil which quickly crystallised. After filtration and washing with dry diethyl ether there was obtained 3-[4-(1,1-dimethyl-2-methoxyethyl)piperidino]prop-1-yne (2.0 g) in the form of white crystals m.p. 152°–154° C.

REFERENCE EXAMPLE 4

A solution of 4-(1,1-dimethyl-2-methoxyethyl)pyridine (10.0 g) in acetic acid (120 ml) was catalytically hydrogenated over platinum dioxide at 40 p.s.i. for 41 hours at from ambient temperature to 43° C. After 24 hours a further quantity of platinum dioxide was added, and a final addition was made after a further 8 hours. After a total of 41 hours the solution obtained after filtration of the catalyst was evaporated in vacuo and further evaporated after the addition of toluene to remove acetic acid. The resultant yellow oil was dissolved in dichloromethane and brought to pH12 with dilute aqueous sodium hydroxide solution. After saturation with sodium chloride, the organic phase was separated and the aqueous layer was re-extracted with five portions of dichloromethane. The combined organic solution was dried over anhydrous magnesium sulphate, and evaporated in vacuo to give 4-(1,1-dimethyl-2-methoxyethyl)piperidine (9.7 g) as a straw-coloured oil.

REFERENCE EXAMPLE 5

A solution of 4-(1,1-dimethyl-2-hydroxyethyl)pyridine (15 g) in dry dimethylformamide (150 ml) was treated with sodium hydride (80% oil dispersion; 3.3 g) under nitrogen at 0° C. with stirring. After 15 minutes at 0° C., this mixture was cooled to −20° C., and a solution of iodomethane (7.4 ml) in dry dimethylformamide (50 ml) was added dropwise during 5 minutes. The mixture which changed from a white to an orange precipitate was allowed to slowly warm to ambient temperature, and stirred overnight under nitrogen. After pouring into excess water, the mixture was extracted with three portions of dichloromethane. The extract was washed with water twice, dried over anhydrous magnesium sulphate and evaporated in vacuo to give a dark oil after further evaporation of added toluene. This oil was chromatographed on silica gel (Merck; 0.04–0.063 mm) under medium pressure using a mixture of dichloromethane and ethyl acetate (2:1) as solvent to give 4-(1,1-dimethyl-2-methoxyethyl)pyridine (11.0 g) as a brown oil.

According to a feature of the present invention, there is provided a method for killing undesired warm-blooded vermin, more particularly rodents, which comprises the oral administration to the animal of an effective lethal amount of at least one compound of general formula I or acid addition salt thereof, more especially for the purpose of controlling or eradicating infestations of rodents, for example rats and mice, e.g. *Rattus rattus, Rattus norvegicus* and *Mus musculus.* Oral administration to the undesired animal of an effective lethal amount of at least one compound of general formula I or acid addition salt thereof may be achieved by the administration of a single large dose of the compound(s) of general formula I or acid addition salt thereof (acute dosing) or, preferably, by the administration of several smaller doses (chronic dosing). When using the compounds of general formula I or acid addition salt thereof to kill undesired warm-blooded vermin, e.g. rodents, the usual standards of care should be applied in avoiding accidental administration to man and domestic animals and wild animals which it is not desired to control or eradicate.

A particularly valuable property of the compounds of general formula I and their acid addition salts, especially when used as rodenticides, is that there is a period of delay, usually about 2 to 9 days, between ingestion and the appearance of symptoms of poisoning and death, during which further amounts may be ingested to lethality during chronic dosing and during which the rodent can leave the vicinity of the place at which ingestion has taken place or the infested area, thereby reducing the risk of suspicion and avoidance of the source of ingestion arising amongst treated and untreated animals.

A further particularly valuable property of the compounds of general formula I and their acid addition salts is that sedation is the major sympton of toxicity and the treated animals die quietly, without exhibiting signs of distress. Although there is a period of delay between ingestion and death, this period is shorter than that experienced with the anticoagulant rodenticides and permits an advantageous reduction in the period of treatment and observation which is necessary to ensure that satisfactory control of an infestation of warm-blooded vermin, particularly rodents, has been achieved.

Anticoagulant rodenticides, for example those of the coumarin type, e.g. warfarin, and those of the indandione type, e.g. chlorophacinone, have been used widely to control or eradicate infestations of rodents, but the appearance in many areas of strains of rodents, particularly rats and mice, which are resistant to anticoagulant rodenticides places increasing limitations on the effectiveness of these anticoagulant rodenticides. The compounds of general formula I and their acid addition salts have been found to be equally as toxic to strains of rodents which are resistant to anticoagulant rodenticides as to strains of rodents which do not possess this resistance. Accordingly, there is provided, as a preferred feature of the present invention, a method for killing rodents, in particular rats and mice, e.g. *Rattus rattus, Rattus norvegicus* and *Mus musculus,* which are resistant to anticoagulant rodenticides, which comprises the oral administration to those rodents of an effective lethal amount of at least one compound of general formula I or acid addition salt thereof. An effective lethal amount of the compounds of general formula I and acid addition salts thereof may, if desired, be administered in undiluted form to the warm-blooded vermin, e.g. rodent, which it is desired to kill, but is more usually administered in the form of liquid or solid orally ingestible compositions, for example toxic baits, comprising the compounds of general formula I or acid addition salts thereof incorporated in or on a suitable ingestible carrier, for example cereals, e.g. vegetable meals, such as oatmeal, flour, e.g. wheat flour, corn starch, bread, cake, grain, seed, fruit, chocolate, animal meal, animal or vegetable oils and fats, e.g. groundnut oil and corn oil, and other known ingestible animal or vegetable materials, e.g. fish and prepared animal food, with or without ingestible additives, for example attractant flavouring substances, binders, antioxidants, surface active agents, e.g. wetting, dispersing or emulsifying agents, and warning colouring substances. Chocolate may be used as a particulary suitable ingestible carrier, either alone or with other ingestible carriers, and sugar may be advantageously used with other ingestible carriers to encourage feeding. Toxic baits may take the natural physical form of the ingestible carrier which is used, e.g. liquids and powders, or may, if desired, be prepared as granules, pills, pellets, tablets or pastes. Toxic baits in liquid, solid or paste form may, if desired, be placed in sachets which may be readily opened by the vermin, e.g. rodents. Toxic baits of suitable physical form, e.g. solid ingestible carriers, e.g. vegetable meal or flour, containing from 2 to 20% of sugar and/or a vegetable or animal oil, or chocolate, may, if desired, be coated on or impregnated into supports comprising small pieces of suitable inert materials, for example blocks or sheets, of wax, wood, synthetic plastics, cardboard or paper, chocolate being a particularly suitable material for coating onto such supports.

Particularly suitable rodenticidal baits comprise from 0.001 to 10% by weight of at least one compound of general formula I or an acid addition salt thereof, from 85 to 98.999% by weight of cereal carrier, from 1 to 5% by weight of a vegetable or animal oil and from 0 to 0.5% by weight of a warning colouring substance.

Orally ingestible compositions according to the present invention may also comprise at least one compound of general formula I or an acid addition salt thereof in association with solid ingestible carriers which are powders, e.g. powdered talc, which may be used as tracking powders. Such tracking powders may be placed in places, particularly runways, habitually frequented and used by rodents, where they adhere to the fur and feet of the rodents and are subsequently ingested orally during grooming.

Liquid and solid orally ingestible compositions according to the present invention preferably comprise 0.001% to 10%, and more especially from 0.05% to 0.2%, by weight of at least one compound of general formula I or an acid addition salt thereof, and may be prepared by incorporating the compounds of general formula I or acid addition salts thereof in undiluted form in or on liquid or solid ingestible carriers or supports, but are preferably prepared by the incorporation in or on ingestible carriers or supports of liquid or solid concentrates containing the compounds of general formula I or acid addition salts thereof. Incorporation of the compounds of general formula I or acid addition salts thereof in undiluted form or in the form of liquid or solid concentrates, in or on ingestible carriers or supports may be achieved by conventional techniques, such as mixing or blending or the incorporation of a solution and removal of the solvent, e.g. by evaporation.

Liquid or solid orally ingestible compositions comprising the compounds of general formula I or acid addition salts thereof incorporated in or on a suitable orally ingestible carrier or support, form a further feature of the present invention and may, in carrying out the method of the present invention, be suitably distributed at loci of vermin infestation.

The method of the present invention may be used, in particular, to protect crop-growing areas, for example cereal crop-growing areas and plantations, e.g. oil-palm plantations, and domestic, agricultural, industrial, commercial and office buildings, for example factories, hospitals, public buildings, storage warehouses, shops, catering establishments and dockyards, and areas in the vicinity of such buildings, and ships against damage by vermin, in particular rodents, e.g. rats and mice.

By the term 'orally ingestible compositions' is meant compositions which are capable of oral ingestion by warm-blooded vermin, e.g. rodents, which are not repellant to aforesaid vermin and which, after ingestion, release lethal amounts of the compounds of general formula I or acid addition salts thereof into the body of the animal. Suitable orally ingestible carriers and supports will possess properties appropriate to the formation of such orally ingestible compositions and will be chemically and physically compatible with the compounds of general formula I or acid addition salts thereof.

Liquid or solid concentrates suitable for use in the preparation of liquid or solid orally ingestible compositions according to the present invention comprising the compounds of general formula I or acid addition salts thereof in association with suitable liquid or solid diluents or carriers, for example solutions, emulsions, syrups, pastes, granules, tablets, pellets or powders, with or without ingestible additives, for example as hereinbefore described, form a further feature of the present invention. Suitable diluents for use in concentrates are liquids or solids which are compatible with the compounds of general formula I and their acid addition salts and the ingestible carrier or support and which do not adversely affect the acceptability of the ingestible carrier or support to the animal or which, in the case of liquid diluents, may be readily removed, e.g. by evaporation, after incorporation of the liquid concentrates in or on the ingestible carrier or support. Suitable solid diluents for use in concentrates according to the present invention include starch, sucrose, lactose, and edible carriers as hereinbefore described. Suitable liquid diluents for use in concentrates according to the present invention include water and animal or vegetable oils and organic solvents, e.g. xylene, isophorone, dioxan or acetone. Liquid concentrates comprising the compounds of general formula I dissolved in solvents which are compatible with the compounds of general formula I and the ingestible carrier or support into or onto which the concentrate is to be incorporated and which does not adversely affect the acceptability of the ingestible carrier or support to the animal, e.g. which is non-repellent to rodents, for example arachis oil, corn oil, xylene, isophorone, dioxan and acetone, are particularly suitable, more especially for the preparation of soild orally ingestible concentrates. Liquid concentrates may also take the form of aqueous or aqueous-organic solutions, suspensions and emulsions, for which purpose acid addition salts of the compounds of general formula I are particularly suitable.

As will be apparent to those skilled in the art, liquid or solid concentrates according to the present invention may be similar in composition to the liquid or solid orally ingestible compositions according to the present invention but containing a higher concentration of the compounds of general formula I or acid addition salts thereof, and may be diluted with further amounts of suitable ingestible carrier or support to give compositions ready for administration to the animals. Liquid and solid concentrates according to the present invention suitable for incorporation in or on orally ingestible carriers or supports preferably comprise from 1% to 90%, and more especially from 1% to 5%, by weight of the compounds of general formula I or acid addition salts thereof.

Where reference is made in the present specification to percentages by weight of the compounds of general formula I and acid addition salts thereof in orally ingestible compositions and concentrates according to the present invention, it is to be understood that such percentages refer to the compound of general formula I content of the acid addition salts.

Liquid or solid rodenticidal concentrates and orally ingestible rodenticidal compositions according to the present invention may also contain the compounds of general formula I or acid addition salts thereof in association, if desired, with one or more rodenticidally active anticoagulant compounds, for example those of the coumarin type, e.g. warfarin, or those of the indandione type, e.g. chlorophacinone.

The following Examples 9 to 15 illustrate rodenticidal compositions according to the present invention.

EXAMPLE 9

A concentrate is prepared by dissolving 1-(3,5-bistrifluoromethylphenyl)-3-[4-(1,1-dimethyl-2-hydroxyethyl)piperidino]prop-1-yne (2 g) in arachis oil (100 ml). This concentrate may be incorporated into an edible bait in amounts of the compounds of from 0.001% to 10%, and preferably from 0.05% to 0.2%, by weight of the total weight of the bait, by admixture with cereal, grain, meal, bran, fruit, vegetables or meat. Such orally ingestible compositions are suitable for use in the control of unwanted rodents.

EXAMPLE 10

A rodenticidal composition is prepared by dissolving 1-(3,5-bistrifluoromethylphenyl)-3-[4-(1,1-dimethyl-2-hydroxyethyl)piperidino]prop-1-yne (1.0 g) in acetone (20 ml), and homogeneously impregnating laboratory rat food pellets (1 kg) to give a toxic bait suitable for use in the control of unwanted rodents.

EXAMPLE 11

1-(3,5-Bistrifluoromethylphenyl)-3-[4-(1,1-dimethyl-2-hydroxyethyl)piperidino]prop-1-yne (5 g) is intimately mixed with a mixture of sucrose (100 g), wheat flour (30 g) and corn starch (70 g). This powdered concentrate is used to coat pieces of scrap meat such as beef and pork, in order to produce a bait for use in the control of unwanted rodents.

EXAMPLE 12

A rodenticidal composition is prepared by intimately mixing 1-(3,5-bistrifluoromethylphenyl)-3-[4-(1,1-dimethyl-2-hydroxyethyl)piperidino]prop-1-yne (1.0 g), oatmeal (899 g), wholemeal flour (50 g) and corn oil (50 g) thoroughly in a blender to achieve uniform distribution of the ingredients throughout the mixture, to give a bait suitable for use in the control of unwanted rodents. If desired, 0.05% by weight of a suitable warning colouring substance, e.g. chlorazol sky blue, may be incorporated in this composition.

EXAMPLE 13

1-(3,5-Bistrifluoromethylphenyl)-3-[4-(1,1-dimethyl-2-hydroxyethyl)piperidino]prop-1-yne (1.0 g), damp coarse oatmeal (949 g) and sugar (50 g) are mixed together throughly in a blender to achieve uniform distribution of the ingredients throughout the mixture, to give a rodenticidal composition in the form of a bait which may be used to control unwanted rodents. If desired, 0.05% by weight of a suitable warning colouring substance, e.g. chlorazol sky blue, may be incorporated in this composition.

EXAMPLE 14

A rodenticidal tracking powder is prepared by intimately mixing 1-(3,5-bistrifluoromethylphenyl)-3-[4-(1,1-dimethyl-2-hydroxyethyl)piperidino]prop-1-yne hydrochloride (1.0 g) and powdered talc (99 g). This powder is placed in runways habitually frequented by rats, where it adheres to the fur and feet of the rats and is subsequently ingested orally by the rats during grooming and kills the rats.

EXAMPLE 15

A concentrate is prepared by intimately mixing 1-(3,5-bistrifluoromethylphenyl)-3-[4-(1,1-dimethyl-2-hydroxyethyl)piperidino]prop-1-yne hydrochloride (90 g) and wholemeal flour (10 g) thoroughly in a blender to achieve uniform distribution through the mixture.

the concentrate thus obtained (100 g) is then intimately mixed with oatmeal (8900 g), wholemeal flour (500) g and corn oil (500) g thoroughly in a blender to give a bait suitable for use in the control of unwanted rodents, in which the ingredients are distributed uniformly throughout the bait.

Similar compositions may be prepared as hereinbefore described in Examples 9 to 15 by replacing 1-(3,5-bistrifluoromethylphenyl)-3-[4-(1,1-dimethyl-2-hydroxyethyl)piperidino]prop-1-yne or its hydrochloride with another salt thereof or another compound of general formula I or acid addition salt thereof.

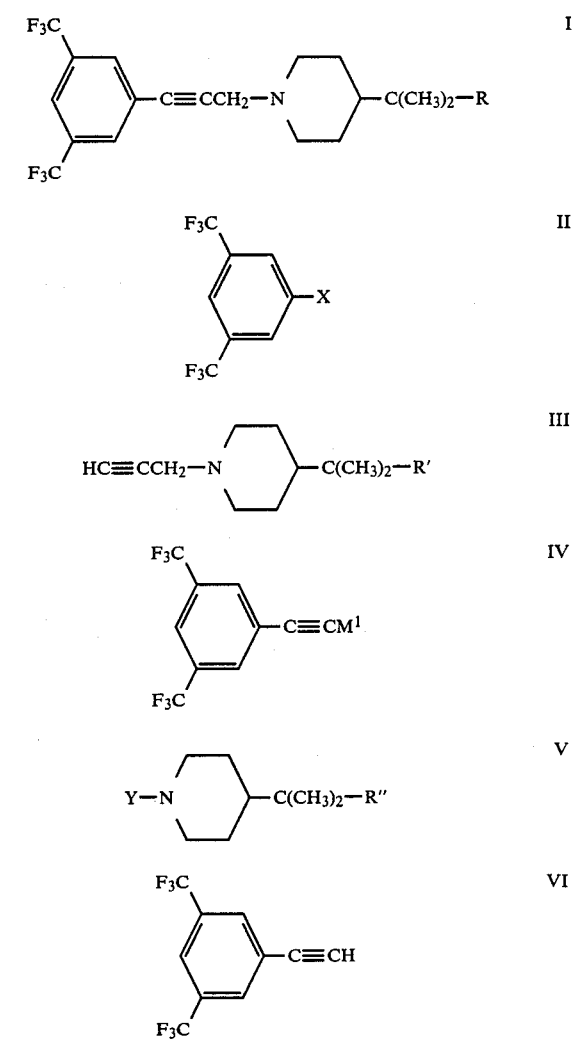

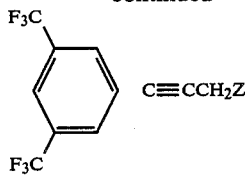

VII

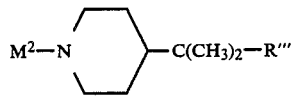

VIII

I claim:

1. A phenylpropargylamine derivative of the formula:

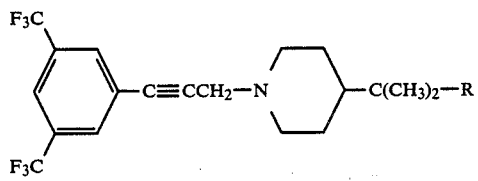

wherein R is a hydroxymethyl group, a straight- or branched-chain alkoxymethyl group containing from 2 to 6 carbon atoms, an unsubstituted or substituted phenoxymethyl group, substituted on the phenyl moiety by one or more substituents selected from halogen, trifluoromethyl, $C_1$-$C_4$ straight- or branched-chain alkyl, and $C_1$-$C_4$ straight- or branched-chain alkoxy, a straight- or branched-chain alkanoyloxymethyl group containing from 3 to 10 carbon atoms, an unsubstituted or substituted benzoyloxymethyl group, substituted on the phenyl moiety by one or more substituents selected from halogen, trifluoromethyl, $C_1$-$C_4$ straight- or branched-chain alkyl, and $C_1$-$C_4$ straight- or branched-chain alkoxy, a straight- or branched-chain alkylsulphonyloxy-methyl group containing from 2 to 9 carbon atoms, an unsubstituted or substituted phenylsulphonyloxymethyl group, substituted on the phenyl moiety by one or more substituents selected from halogen, trifluoromethyl, $C_1$-$C_4$ straight- or branched-chain alkyl, and $C_1$-$C_4$ straight- or branched-chain alkoxy, a formyl group, an unsubstituted or substituted aminomethyl group, substituted by one or two straight- or branched-chain alkyl groups, which may be the same or different and each said alkyl group contains from 1 to 4 carbon atoms, or a hydroxyaminomethyl group; and acid addition salts thereof.

2. A compound according to claim 1, wherein R represents the hydroxymethyl group, a straight- or branched-chain alkoxymethyl group containing from 2 to 6 carbon atoms, a straight- or branched-chain alkanoyloxymethyl group containing from 3 to 7 carbon atoms, a substituted or unsubstituted benzoyloxymethyl group, a straight- or branched-chain alkylsulphonyloxymethyl group containing from 2 to 6 carbon atoms, a formyl group or a hydroxyiminomethyl group.

3. A compound according to claim 1 which is 1-(3,5-bistrifluoromethylphenyl)-3-[4-(1,1-dimethyl-2-hydroxyethyl)piperidino]prop-1-yne.

4. A compound according to claim 1 which is 1-(3,5-bistrifluoromethylphenyl)-3-[4-(1,1-dimethyl-2-methoxyethyl)piperidino]prop-1-yne.

5. A compound according to claim 1 which is 1-(3,5-bistrifluoromethylphenyl)-3-[4-(1,1-dimethyl-2-acetyloxyethyl)piperidino]prop-1-yne.

6. A compound according to claim 1 which is 1-(3,5-bistrifluoromethylphenyl)-3-[4-(1,1-dimethyl-2-oxoethyl)piperidino]prop-1-yne.

7. An acid addition salt of a compound according to any one of claims 1 to 7.

8. A method for killing undesired warm-blooded vermin which comprises the oral administration to the animal of an effective lethal amount of a phenylpropargylamine derivate claimed in claim 1 or an acid addition salt thereof.

9. A method according to claim 8 in which the vermin are rodents.

10. A method according to claim 9 in which the rodents are rats or mice.

11. A method according to claim 9 or 10 in which the rodents are resistant to anticoagulant rodenticides.

12. A composition for oral ingestion by, and killing of, undesired warm-blooded vermin which comprises a phenylpropargylamine derivative claimed in claim 1, or an acid addition salt thereof, incorporated in or on a carrier or support suitable for ingestion by vermin.

13. A liquid or solid composition according to claim 12 which comprises from 0.001% to 10% by weight of a phenylpropargylamine derivative claimed in claim 1 or an acid addition salt thereof.

14. A liquid or solid composition according to claim 12 which comprises from 0.05% to 0.2% by weight of a phenylpropargylamine derivative claimed in claim 1 or an acid addition salt thereof.

15. A liquid or solid concentrate suitable for incorporation in or on carriers or supports orally ingestible by warm-blooded vermin, which comprises from 1% to 90% by weight of a phenylpropargylamine derivative claimed in claim 1 or an acid addition salt thereof.

16. A liquid or solid concentrate suitable incorporation in or on carriers or supports orally ingestible by warm-blooded vermin, which comprises from 1% to 5% by weight of a phenylpropargylamine derivative claimed in claim 1 or an acid addition salt thereof.

17. A composition according to any one of claims 12 to 16 which includes, in addition, one or more rodenticidally active anticoagulant compounds of the coumarin or indandione type.

* * * * *